United States Patent [19]

Croll

[11] Patent Number: 4,640,685
[45] Date of Patent: Feb. 3, 1987

[54] HAND-HELD LIGHT FILTER

[76] Inventor: Theodore P. Croll, 685 S. Chubb Dr., Doylestown, Pa. 18901

[21] Appl. No.: 723,332

[22] Filed: Apr. 15, 1985

[51] Int. Cl.$^4$ ................................................ A61C 3/00
[52] U.S. Cl. .................................... 433/141; 433/229; 250/515.1; 350/1.1; 350/318; 350/311
[58] Field of Search ................ 433/229, 141; 350/1.1, 350/318, 246, 256, 311; 250/515.1

[56] References Cited

U.S. PATENT DOCUMENTS

| | | | |
|---|---|---|---|
| 1,938,734 | 12/1933 | Withrow | 350/1.1 |
| 2,392,671 | 1/1946 | Husted | 350/318 |
| 3,409,348 | 11/1968 | Annis et al. | 350/256 |

Primary Examiner—John J. Wilson
Assistant Examiner—Adriene J. Lepiane
Attorney, Agent, or Firm—Gregory J. Gore

[57] ABSTRACT

The invention discloses a protective light shield to reduce the harmful effects of resin-curing lights used in dentistry. This is a shield made principally of a single sheet of filtering plastic, shaped in a convenient paddle configuration. The dimension of the filter-paddle is sufficient to block all direct and reflected light from the tooth of the patient that would possibly be seen by any personnel in the operatory. A portion of the paddle is provided with a magnifier which may be employed by the physician for closer inspection of the tooth being operated on. Additionally, a relatively thin intensity-filtering material is applied to the back of the light paddle so that the intensity of the filtered light is reduced for the increased comfort and protection of the physician.

7 Claims, 3 Drawing Figures

HAND-HELD LIGHT FILTER

FIELD OF THE INVENTION

This invention relates generally to hand-held instruments used in dental medicine. More specifically, this invention relates to protective shields employed to filter out harmful light frequencies emitted by the type of light used in the curing process of modern dental bonding materials.

BACKGROUND OF THE INVENTION

The advent of modern bonding materials used in dentistry has brought with it the problem of eye exposure to the resin curing lights. These types of curing lights emit wave lengths that have been shown to be damaging to the human eye. The need for protective apparatus for both the physician and assistant staff members has been recognized. The protective devices employed in the past include light-filtering lenses, either worn over the eyes in the form of eyeglasswear or small hand-held instruments that are held close to the region to the tooth being cured. The dangerous range of UV output that has been identified is in the 400 to 525 nanometer range.

Prior art examples of hand-held light filtering instruments have had the disadvantages of; being too small for the patient to hold, not filtering the proper wave lengths of light sufficiently, not being able to be sterilized in a commonly used disinfectant, not providing any additional magnification and not adequately filtering the intensity of the light transmitted through the filter.

In addition to the problems with prior art protective filtering devices, there are several additional needs which have not been met. Shielding the eyes with eyeglasswear requires a separate set of glasses for each individual present in the operatory. This results in the increased cost of requiring many pairs of protective eyewear as well as the inconvenience and discomfort to other staff members. There is a need for a single, inexpensive unit which provides protection for all of the type described in the present application. Furthermore, tests have shown that after approximately 2 minutes of use of the tinted eye shield devices, the physician's eyes become color distorted and require color correcting. The remedy for providing the necessary color correction is for the physician to concentrate his vision on a light blue color source which, after a few seconds, will correct his vision for color. Heretofore, there has not been a convenient source of the light blue color correcting object and this is provided in the instant invention as a colored portion on the hand-held filtering instrument itself which, of course, is present at exactly the times when the physician would require vision color correcting.

OBJECTS & SUMMARY OF THE INVENTION

Accordingly, it is a principal object of the present invention to provide an improved hand-held light filter which will conveniently and inexpensively shield all personnel within an operatory from the harmful effects of UV light waves emitted from resin-curing lights with a single device.

It is another object of the invention to provide the hand-held filter with sufficient dimension and functional shape so that the instrument is easy to use, yet provides the extent of coverage required for proper shielding of all staff present in the operatory.

It is an additional object of the present invention to include in a hand-held light shield a portion of that shield containing magnification properties to further assist the vision of the operating physician.

It is a further object of the instant invention to include in a hand-held light shield, an intensity filter to reduce the amount of filtered light which passes through the filter to aid the comfort of the operating physician.

And, finally, an additional object of the invention is to include in the hand-held unit an area which is colored so that the operating physician may use this as a convenient vision color-correcting instrument.

The foregoing and other objects and advantages are accomplished according to the details in construction of the instant invention as described further herein which include a shield made principally of a single sheet of filtering plastic, shaped in a convenient paddle configuration. The dimension of the filter-paddle is sufficient to block all direct and reflected light from the tooth of the patient that would possibly be seen by any personnel in the operatory. A portion of the paddle is provided with a magnifier which may be employed by the physician for closer inspection of the tooth being operated on. Additionally, a relatively thin intensity-filtering material is applied to the back of the light paddle so that the intensity of the filtered light is reduced for the increased comfort and protection of the physician. Furthermore, a light blue panel is provided across the end portion of the panel to provide a convenient source of color-correcting light for the physician's vision. The blue panel may be applied to the paddle in a variety of ways. The material used in constructing the elements of the panel are such that it may be placed in disinfectant without damage to the instrument.

DESCRIPTION OF THE PREFERRED EMBODIMENT

Figure 1:
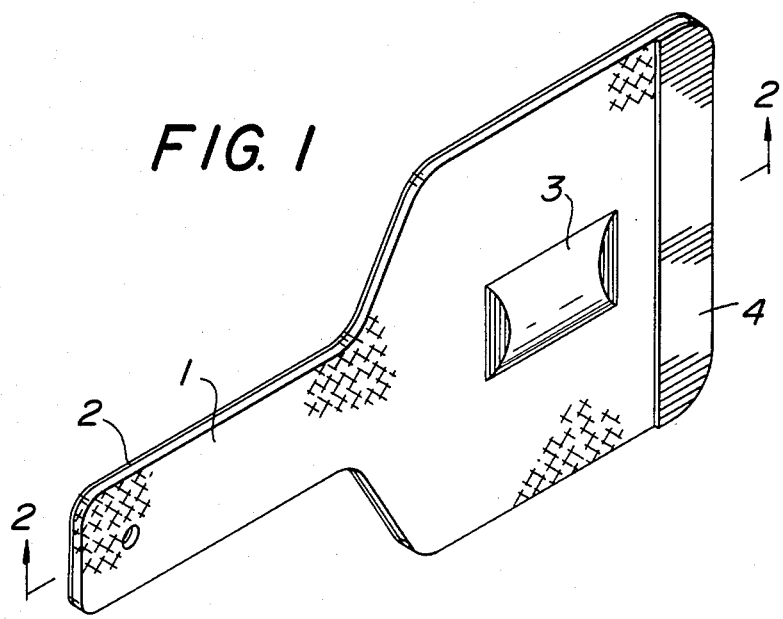
FIG. 1 is a perspective view of the light filter.
Figure 2:
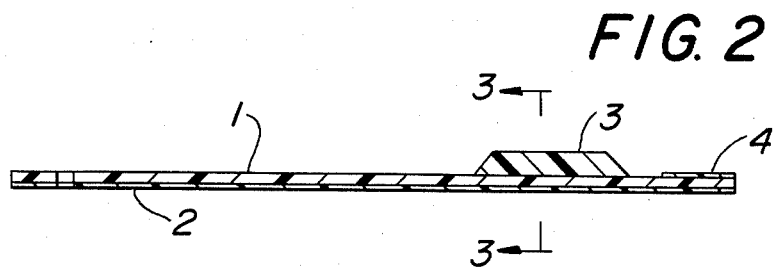
FIG. 2 is a top view of the instant invention.
Figure 3:
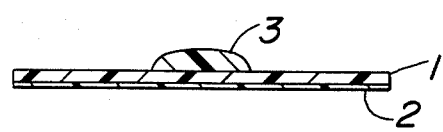
FIG. 3 is a sectional view taken from FIG. 2 showing the three-layer construction of the light filter.

The present invention employs inexpensive and simple construction. All parts of the invention are made from readily available plastic and are attached with suitable, optically-neutral bonding materials. FIG. 1 shows the main paddle element being formed of an orange "Plexiglas"(TM) material that is effective in filtering out light rays in the range of 400 to 525 nanometers. This material may be of the type produced by the Rohm & Haas Company of Bristol, Pa., sold as "Plexiglas G - Orange", a polymethyl methocrylate, in the thickness of approximately $\frac{3}{8}$ inch. This material has been shown to filter out 100% of light waves in the 400–525 nanometer range.

An intensity filter 2 may be fixed to the main paddle element. This material may be any tinted plastic as may be desired to reduce the intensity of the light transmitted through the filter. Applicant has used a smoke-gray color with good results. Magnifying element 3 is affixed to the central portion of the main paddle to be used by the physician when magnification is deemed necessary. The magnifying element has been contained to a small portion of the paddle. If it is not desired to have magnification, the physician may move the shield so that the area of visual concentration is away from the magnifier but through a different portion of the filter. Color correcting strip 4 is located at the end of the panel and is sky blue in color. The strip is intended to be a point of visual concentration for the physician in order that his vision may be color corrected. The main paddle element is flat and includes a handle portion within its shape to aid in the economy of manufacture.

Magnification element 3 is similarly made of plastic or glass, but may be of any configuration known in the optical arts to provide sufficient magnification and depth of field as may be desired.

It should be understood that there may be modifications and adaptations of the specific embodiment of the present invention described herein and still fall within the scope and spirit of the invention. It is therefore intended that the scope of the invention be determined by the appended claims and their legal equivalents.

What is claimed is:

1. A hand-held light shield device for use in dentistry, comprising:
   a. a main paddle element which has optical properties necessary to filter out physically harmful light,
   b. an intensity filter affixed to one side of said main paddle element,
   c. a magnifying element on said main paddle portion, and
   d. a light blue colored strip affixed to the end of said main panel portion.

2. The light filter described in claim 1 further including a narrowed portion of the main paddle element suitable for use as a handle.

3. The hand-held light filter, as described in claim 2, wherein the main paddle element is approximately $\frac{1}{8}$-inch thick.

4. The light filter described in claim 3 wherein the main paddle element is made of plastic.

5. The hand-held light filter described in claim 4 wherein said intensity filter is co-extensive with said main paddle portion.

6. The hand-held light shield device as described in claim 5 wherein the main paddle portion filters out a high percentage of ultraviolet light rays in the 400–525 nanometer range.

7. The light filter, as described in claim 6, further described in that the overall dimension of said light filter is no greater than 6"×10" and no less than 4"×8".

* * * * *